(12) United States Patent
Fonseca et al.

(10) Patent No.: US 6,409,683 B1
(45) Date of Patent: Jun. 25, 2002

(54) MEDICAL GUIDEWIRE WITH IMPROVED COIL ATTACHMENT

(75) Inventors: Dennis J. Fonseca, Miami; Brian G. Gore, Orlando, both of FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/399,710

(22) Filed: Sep. 21, 1999

Related U.S. Application Data

(60) Provisional application No. 60/102,446, filed on Sep. 30, 1998.

(51) Int. Cl.[7] ................................................. A61B 5/00
(52) U.S. Cl. ........................................................ 600/585
(58) Field of Search ................................. 606/200, 191, 606/194, 195, 198, 159; 600/585, 434; 604/170.01

(56) References Cited

U.S. PATENT DOCUMENTS

| | | |
|---|---|---|
| 3,906,938 A | 9/1975 | Fleischhacker |
| 4,044,765 A | 8/1977 | Kline |
| 4,538,622 A | 9/1985 | Samson et al. |
| 4,545,390 A | 10/1985 | Leary |
| 4,773,432 A | 9/1988 | Rydell |
| 4,798,598 A | 1/1989 | Bonello et al. |
| 4,815,478 A | 3/1989 | Buchbinder et al. |
| 4,846,186 A | 7/1989 | Box et al. |
| 4,848,342 A | 7/1989 | Kaltenbach |
| 5,069,674 A | 12/1991 | Fearnot et al. |
| 5,147,317 A | 9/1992 | Shank et al. |
| 5,259,393 A | 11/1993 | Corso, Jr. et al. |
| 5,433,200 A | 7/1995 | Fleischhacker, Jr. |
| 5,460,187 A | 10/1995 | Daigle et al. |
| 5,514,128 A | 5/1996 | Hillsman et al. |

*Primary Examiner*—Kevin T. Truong
(74) *Attorney, Agent, or Firm*—Henry W. Collins

(57) ABSTRACT

A medical guidewire which is comprised of an elongated corewire having a tapered distal section and a coiled wire spring positioned over the distal section and extending onto and bonded to the uniform corewire section proximal the tapered section. The turns of the corewire spring which are bonded to the periphery of the uniform section of the corewire are very widely spaced apart to thereby lock onto the corewire and thereby resist the detachment of the coiled wire spring from the corewire.

4 Claims, 2 Drawing Sheets

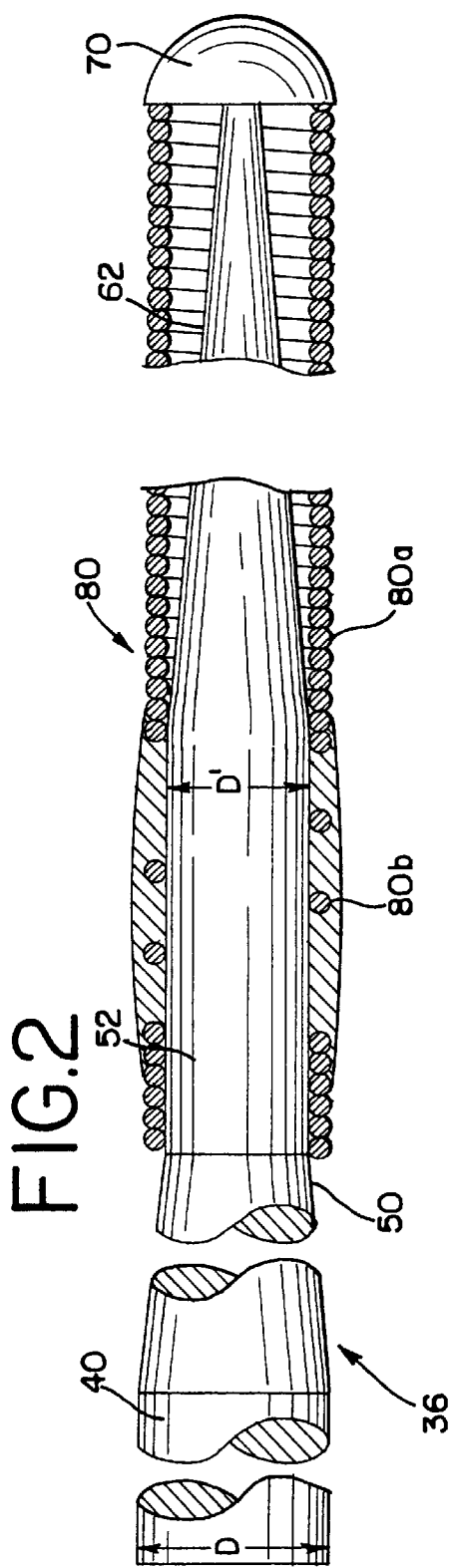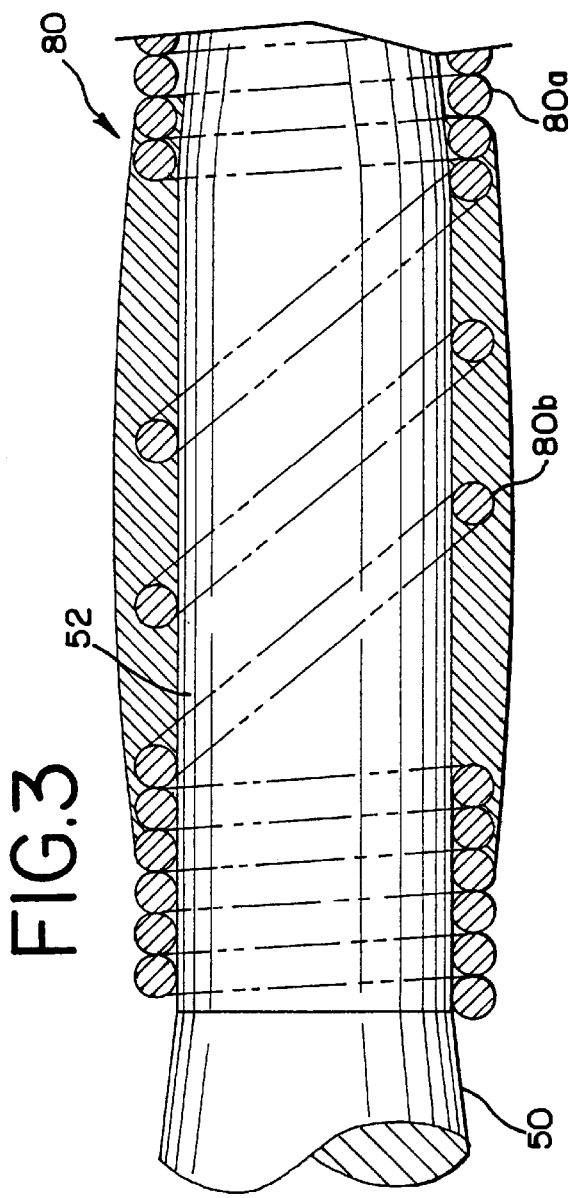

MEDICAL GUIDEWIRE WITH IMPROVED COIL ATTACHMENT

This application claims benefit to Provisional Application No. 60/102,446 filed Sep. 30, 1998.

BACKGROUND OF THE INVENTION

1. Field of the Invention

The present invention relates to a medical guidewire which may be used, for example, to position a catheter, or a balloon catheter, within the vasculature of the human body.

2. Description of the Prior Art

Percutaneous angioplasty is a therapeutic medical procedure which can increase blood flow through a blood vessel. This procedure may sometimes be used as an alternative to coronary by-pass surgery. An elongated catheter having a deflated balloon at its distal end is guided through the cardiovascular system to the coronary artery of the heart. The balloon is inflated to compress deposits that have accumulated along the inner walls of the coronary artery to thereby widen the artery lumen and increase blood flow.

A known technique for positioning a balloon catheter uses an elongated guidewire which is inserted into a patient and routed through the cardiovascular system. The guidewire progress is viewed on an X-ray imaging screen.

Representative prior art patents which disclose flexible, elongated guidewires are U.S. Pat. No. 4,545,390 to Leary; U.S. Pat. No. 4,538,622 to Samson, et al.; U.S. Pat. No. 3,906,938 to Fleischhacker; U.S. Pat. No. 4,846,186 to Box, et al.; and U.S. Pat. No. 5,259,393 to Corso Jr., et al. The latter two patents, assigned to the same assignee as the present applications, are incorporated herein by reference.

One problem with currently available guidewires occurs when the guidewire is being removed from the vasculature of the human body. The coil may become partially detached from the distal end of the guidewire and begin to unravel as the guidewire is being withdrawn with the result that it is possible for the coil to become separated from the corewire of the guidewire. Numerous techniques have been developed to prevent the detachment of the coil from the corewire including various arrangements in which the coil is spot welded to the corewire at the distal tip of the corewire and at least two or three locations along the periphery of the corewire. However, with a continues relatively tight wound coil it is still possible that the coil may become detached from the corewire at one position along the corewire and the helically wrapped coil tends to unwind with the result that the coil is completely released from the corewire along its entire length.

SUMMARY OF THE INVENTION

The present invention is directed toward a medical guidewire which includes an elongated corewire having proximal and distal ends and having a first, uniform diameter, proximal portion and a second, more flexible, reduced diameter distal portion. The guidewire also includes a coiled wire spring having distal and proximal ends and including a distal portion comprised of tightly spaced coil turns and a proximal portion comprised of very loosely spaced coil turns. The coiled wire spring is bonded, for example by welding, to the distal tip of the corewire and is also similarly attached to the uniform diameter portion of the corewire over the entire portion of the coiled wire spring which is comprised of loosely spaced coil turns.

The loosely spaced coil turns are very widely spaced from each other in order to cause the coil wire in the region of the loosely spaced turns to extend along the corewire in a direction approaching being longitudinal with respect to the axis of the corewire. Accordingly, in the event the corewire spring becomes detached from the corewire at the distal tip of the corewire, the coil may then begin to unwind over the tightly wound section of the coil spring, but the very loosely spaced coil turns tend to tighten or clamp down on the corewire and thereby function much as a "Chinese finger gripper." This gripping on the corewire prevents further unraveling and total detachment of the wire spring from the corewire. This is an important safety feature which largely resists detachment of the coil spring from the corewire.

In accordance with another aspect of the present invention, the coiled corewire is formed of a wire having a cylindrical cross section of a predetermined diameter and adjacent turns of the loosely spaced coiled turns are spaced apart at least three times the diameter of the wire of the coiled wire spring.

In accordance with still another aspect of the present invention, the adjacent turns of the loosely spaced coiled turns are spaced apart at least about five times the diameter of the wire of the coiled wire spring, or alternatively, the adjacent turns of the loosely spaced coiled turns are spaced apart at least about seven times the diameter of the coiled wire spring.

In accordance with still another aspect of the present invention, the coiled wire spring is formed of a wire having a cylindrical cross section with a predetermined diameter, preferably about 0.0025 of an inch, and in which adjacent turns of the loosely spaced coil are spaced apart at least about 0.0125 of an inch. Alternatively, the adjacent turns of the loosely spaced coil are spaced apart at least about 0.0175 of an inch.

Again, if the distal end of the coiled wire spring becomes detached from the distal end of the corewire and the helically wound coil wire spring begins to unwind from the corewire as the distal end of the wire spring is pulled longitudinally, the very loosely spaced coiled turns which extend in a direction approaching that of being longitudinal to the axis of the corewire, serve the function of locking unto the corewire in a manner somewhat analogous to a "Chinese finger gripper" to thereby prevent further unraveling of the coiled wire from the corewire. Again, this important safety feature significantly prevents detachment of the coil from the corewire.

BRIEF DESCRIPTION OF THE DRAWINGS

FIG. 2 is an elevation segmented view of a flexible guidewire constructed in accordance with the invention; and FIG. 3 is an elevational expanded view of a section of the guidewire shown in FIG. 2.

DESCRIPTION OF A PREFERRED EMBODIMENT

Figure 1:
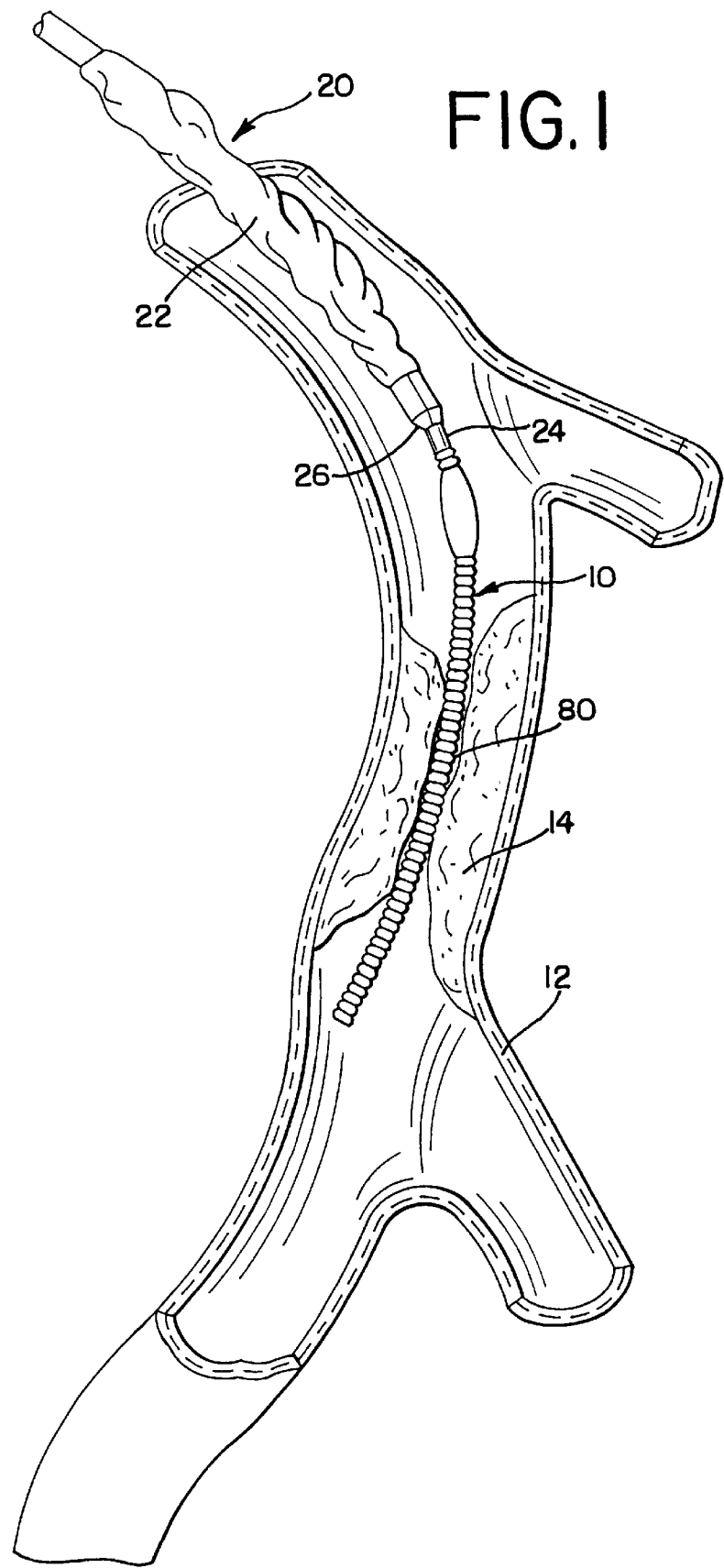
FIG. 1 is a diagrammatic view showing a blood vessel that has been occluded with deposits along an inner wall and shows the positioning of a flexible guidewire within the blood vessel.

Turning now to the drawings, FIG. 1 illustrates a distal portion of a flexible, small diameter guidewire 10 that can be guided through a patient cardiovascular system. A distal end of the guidewire is shown in FIG. 1 bridging a region in a blood vessel 12 having occlusions 14 which restrict blood flow through the blood vessel 12. The guidewire 10 is long enough to be routed from a patient entry point through the patient to the obstructed blood vessel region. In a preferred embodiment the guidewire has a length of 175 centimeters. As the guidewire 10 is inserted along the tortuous path to the obstructed blood vessel region, an attending physician conducting the procedure monitors progress of the guidewire 10 on an X-ray imaging viewing screen.

The FIG. 1 depiction illustrates use of a guidewire for routing a balloon catheter 20 to the vicinity of an obstruction 14. The balloon catheter 20 includes a passageway, or lumen, that extends from a proximal location outside the patient to a distally located balloon 22. Fluid is routed into the catheter through the lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned within the subject, the catheter 20 can be slid over the guidewire.

The distal tip portion of the guidewire 10 is flexible and can be bent to a predetermined configuration to facilitate routing the guidewire 10 along the cardiovascular system to the FIG. 1 region of the blood vessel 12. The pre-bent tip can be re-oriented by the physician. Torques applied to the proximal end of the guidewire are transmitted along the length of the guidewire and re-orient the distal tip to point in a desired direction.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

The guidewire 10 is constructed to include a helically wound coil spring 80 of controlled radiopaqueness that appears when the blood vessel 12 is monitored on a viewing screen. This radiopacity allows adequate tracing of the guidewire while minimizing interference with a post procedure angiogram.

Turning now to FIGS. 2 and 3, the guidewire 10 is seen to include a center stainless steel corewire 36 having a first or proximal uniform diameter portion 40 having a diameter D, in the range 0.010–0.038 of an inch, extending well over half the length of the guidewire. The total length of the uniform diameter portion 40 is approximately 148 centimeters of the total guidewire length of 175 centimeters. The guidewire is typically covered with a suitable lubricious coating.

At the distal end of the guidewire, the corewire 36 tapers along a segment 50 uniformly to a segment 52 having a uniform diameter D'. The corewire 36 again tapers uniformly along a segment 62 that has a length of approximately 1 inch and can be pre-bent to a particular configuration by the attending physician to facilitate insertion of the guidewire within the subject.

At the extreme distal tip portion of the guidewire 10, a weld 70 or other means of attachment, such as brazing, attaches a spring 80 to the corewire 36. The weld or braze 70 defines a smooth hemispherical bead which does not damage the inner lining of the blood vessels as the guidewire tip comes in contact with those linings.

The helically wound coil spring 80 is preferably formed of a material such as platinum, which exhibits the characteristic of being highly visible when viewed under X-ray radiation.

The distal coil turns 80a of the spring 80 are closely packed along the tapered core segment 62 so that adjacent coil turns 80a of the distal coil section 81a are separated by a spacing or pitch distance of about 0.001 of an inch. The coil turns of the proximal coil section 80b of the spring 80 overlying the uniform diameter segment 52 are very widely spaced i.e. on the order of between about 0.0125 and 0.025 of an inch with an optimum spacing between turns of about 0.0175 of an inch. The proximal coil section 80b is bonded to the corewire over the entire length of this coil section 80b. Various methods may be used to bond or attach the coil sections to the corewire including, but not limited to, soldering, brazing or various combinations thereof. The corewire 36 is constructed from a uniform diameter stainless steel wire which is preferably centerless ground along the tapered section 50 to the reduced diameter segment 52 and again ground along the tapered section 62. While not shown in the drawings, the distal end of the tapered section 62 may be flattened by rolling or stamping to further increase the flexibility of the tip of the guidewire.

The guidewire 10 depicted in FIGS. 2 and 3 is particularly suited for insertion into small diameter blood vessels and may be used, for example, for positioning a balloon catheter in a bridging relationship within the coronary vessel.

The dimensions mentioned in this specification are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

That which is claimed is:

1. A medical guidewire comprising:

an elongated corewire having proximal and distal ends and having a first, uniform diameter proximal portion and a second flexible, reduced diameter distal portion;

a coiled wire spring having distal and proximal ends and including a distal portion comprised of tightly spaced coil turns and a proximal portion comprised of loosely spaced coil turns, said coiled wire spring is formed of a wire having a cylindrical cross section of a predetermined diameter and in which adjacent turns of the loosely spaced coil turns are spaced apart at least five times the diameter of the wire in the coiled wire spring;

bonding means for attaching the distal end of the coiled wire spring to the distal end of the corewire; and, bonding means for attaching the entire portion of the coiled wire spring comprised of the loosely spaced coil turns to the uniform diameter portion of the corewire.

2. A medical guidewire as defined in claim 1, in which the coiled wire spring is formed of a wire having a cylindrical cross section of a predetermined diameter and in which adjacent turns of the loosely spaced coil turns are spaced apart at least seven times the diameter of the wire in the coiled wire spring.

3. A medical guidewire as defined in claim 1, in which the coiled wire spring is formed of a wire having a cylindrical cross section of approximately 0.0025 of an inch and in which adjacent turns of the loosely spaced coil are spaced apart at least about 0.0125 of an inch.

4. A medical guidewire as defined in claim 1, in which the coiled wire spring is formed of a wire having a cylindrical cross section of approximately 0.0025 of an inch and in which adjacent turns of the loosely spaced coil are spaced apart at least about 0.0175 of an inch.

\* \* \* \* \*